United States Patent
Huang et al.

(10) Patent No.: US 10,582,711 B2
(45) Date of Patent: Mar. 10, 2020

(54) METHOD FOR IMPARTING TO AN ARTICLE OR PRODUCT ANTIMICROBIAL ACTIVITY AND THE ARTICLE OR PRODUCT HAVING THE ANTIMICROBIAL ACTIVITY

(71) Applicant: Leader Optronics Technology Co., Ltd., Tainan (TW)

(72) Inventors: Yu-Hui Huang, Kaohsiung (TW); Shyh-Haur Su, Tainan (TW)

(73) Assignee: LEADER OPTRONICS TECHNOLOGY CO., LTD., Tainan (TW)

(*) Notice: Subject to any disclaimer, the term of this patent is extended or adjusted under 35 U.S.C. 154(b) by 0 days.

(21) Appl. No.: 15/264,995

(22) Filed: Sep. 14, 2016

(65) Prior Publication Data

US 2017/0086462 A1 Mar. 30, 2017

(30) Foreign Application Priority Data

Sep. 25, 2015 (TW) .............................. 104131892 A

(51) Int. Cl.
*A01N 55/00* (2006.01)
*A01N 25/12* (2006.01)
*A01N 25/34* (2006.01)

(52) U.S. Cl.
CPC ............. *A01N 55/00* (2013.01); *A01N 25/12* (2013.01); *A01N 25/34* (2013.01)

(58) Field of Classification Search
None
See application file for complete search history.

(56) References Cited

U.S. PATENT DOCUMENTS

| | | | | |
|---|---|---|---|---|
| 5,789,517 A * | 8/1998 | Ochiai | ................. | C08G 77/06 524/837 |
| 8,314,201 B2 * | 11/2012 | Meador | ................. | C04B 35/14 423/335 |
| 2005/0133174 A1 * | 6/2005 | Gorley | ................. | A47L 13/16 162/108 |
| 2007/0111539 A1 * | 5/2007 | Kon | ................. | C09D 183/04 438/778 |
| 2007/0116783 A1 * | 5/2007 | Ono | ................. | A01N 59/16 424/618 |
| 2009/0214618 A1 * | 8/2009 | Schoenfisch | ................. | A61K 9/167 424/426 |
| 2012/0134951 A1 * | 5/2012 | Stasko | ................. | A61K 9/0014 424/78.06 |
| 2013/0108702 A1 * | 5/2013 | Santra | ................. | A01N 59/20 424/490 |

FOREIGN PATENT DOCUMENTS

| | | | | |
|---|---|---|---|---|
| CN | 102504264 A | * | 6/2012 | |
| EP | 2832802 A1 | * | 2/2015 | ............. A61L 27/34 |

OTHER PUBLICATIONS

Shin et al. Journal of the American Chemical Society 2007 129:4612-4619.*
Wu et al. Journal of Polymer Science Part B: Polymer Physics 2011 49:566-573.*
Beer et al. Toxicology Letters 2012 208:286-292.*
Mod et al. Journal of the American Chemical Society 2003 125:3172-3713 (Year: 2003).*
Mod et al. Macromolecules 2004 37:5228-5238 (Year: 2004).*
Jang et al. (Journal of Sol-Gel Science and Technology 2007 41:19-24 (Year: 2007).*
Chen et al. ACS Applied Materials and Interfaces 2011 3:1154-1162 (Year: 2011).*
Zhu et al. Langmuir 2012 28:416-423 (Year: 2012).*
Fernandes et al. Food Hydrocolloids 2014 35:247-252 (Year: 2014).*
Rosenholm et al. Journal of Controlled Release 2008 128:157-164 (Year: 2008).*
Nutrient Broth Product Information 2013 one page (Year: 2013).*
Shin et al. Chemistry of Materials 2008 20:239-249 (Year: 2008).*
Roche et al. Thin Solid Films 2010 518:3640-3645 (Year: 2010).*
Kneuer et al. International Journal of Pharmaceutics 2000 196:257-261 (Year: 2000).*
Jiang et al. Journal of Nanoparticle Research 2009 11:77-89 (Year: 2009).*

* cited by examiner

*Primary Examiner* — Robert A Wax
*Assistant Examiner* — Caralynne E Helm
(74) *Attorney, Agent, or Firm* — Hamre, Schumann, Mueller & Larson, P.C.

(57) ABSTRACT

A method for imparting to an article or product antimicrobial activity includes a step of applying an antimicrobial agent containing an antimicrobial polyaminosilane to the article or product. The antimicrobial polyaminosilane is prepared by subjecting an aminosilane monomer to a hydrolysis and condensation reaction. The antimicrobial polyaminosilane thus prepared is free of halide ions.

7 Claims, No Drawings

METHOD FOR IMPARTING TO AN ARTICLE OR PRODUCT ANTIMICROBIAL ACTIVITY AND THE ARTICLE OR PRODUCT HAVING THE ANTIMICROBIAL ACTIVITY

CROSS-REFERENCE TO RELATED APPLICATIONS

This application claims priority of Taiwanese Application No. 104131892, filed on Sep. 25, 2015.

FIELD

The disclosure relates to a method for imparting an article or a hygiene product with antimicrobial activity. The disclosure also relates to the article and the hygiene product imparted with the antimicrobial activity.

BACKGROUND

There are many bacteria and viruses existing in daily environment, especially in hospitals, schools, and other public places. In addition, touch type electronic products are widely used nowadays and may become breeding grounds where bacteria and viruses are easily bred and propagated. In view of the aforesaid, it is required to use antimicrobial products having bacteriostatic and/or bactericidal activities to reduce breeding of microbes such as bacteria and viruses so as to improve living environments and to maintain health.

There are various antimicrobial products which have different antimicrobial mechanisms. Commercially available antimicrobial products are typically classified into three categories, i.e., natural antimicrobial agents, inorganic antimicrobial agents, and organic antimicrobial agents.

Specifically, the natural antimicrobial agents are produced by extracting specific ingredients from natural sources, such as chitin, mustard, wasabi, or the like. The natural antimicrobial agents have relatively pure components and may be conveniently used. However, they have a low sterilizing rate and a limited antimicrobial activity, and are also inferior in heat resistance such that they have short service life and thus may not be used for a long period of time.

The inorganic antimicrobial agents made from various metals (for example, silver, copper, or zinc), which are immobilized on a porous material via physical adsorption or ion exchange. For example, US 2014/0017462 discloses an antimicrobial glass article which comprises a glass substrate and copper-containing nanoparticles (such as Cu, CuO, or $Cu_2O$ nanoparticles) on a surface of the glass substrate. However, the appearance of the product such as the antimicrobial glass article may be undesirably tainted by the intrinsic color of the metal or metal ion. In addition, although silver ions have a superior antimicrobial effect and are most popularly used in the inorganic antimicrobial agents, they are costly and are liable to discoloration due to oxidation of the silver ions in use.

The organic antimicrobial agents include acylanilides, quaternary ammonium salts, phenols, and the like. The antimicrobial mechanism for the quaternary ammonium salts involves taking the advantage of easy combination of the positive charged ammonium ions contained in the quaternary ammonium salts with the negatively charged microbes so as to disrupt cell walls and/or cell membranes of the microbes, thus achieving an effect of killing or inhibiting the microbes. For example, it is described in the background of U.S. Pat. No. 5,959,014 that the antimicrobial agent having a quaternary ammonium group is synthesized by subjecting dimethylalkyl tertiary amine and chloropropyl trimethoxysilane to a reaction. The mechanism of the reaction is shown below:

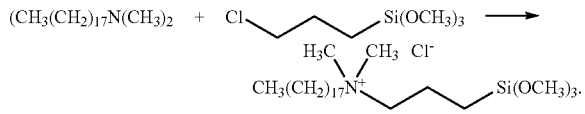

However, since the antimicrobial agent contains chloride ions, it is liable to production of toxic chlorine gas when the antimicrobial agent is used at an elevated temperature. The chlorine gas is not only strongly hazardous to human health but also liable to production of oncogenic organic chloride, such as trichloromethane.

It is described in an article entitled *"Process and Mechanism of Surface Modification of Silica with Silane Coupling Agent APTS"* by Bing Qiao et al., Department of Chemical Engineering, Tsinghua University, Beijing, China, in CIESC Journal (July 2014) to modify surface of silica using gamma aminopropyltriethoxysilane (APTS). It is disclosed in the article that APTS may be subject to a hydrolysis in the presence of water which is followed by a condensation reaction to form a polysiloxane, as shown below.

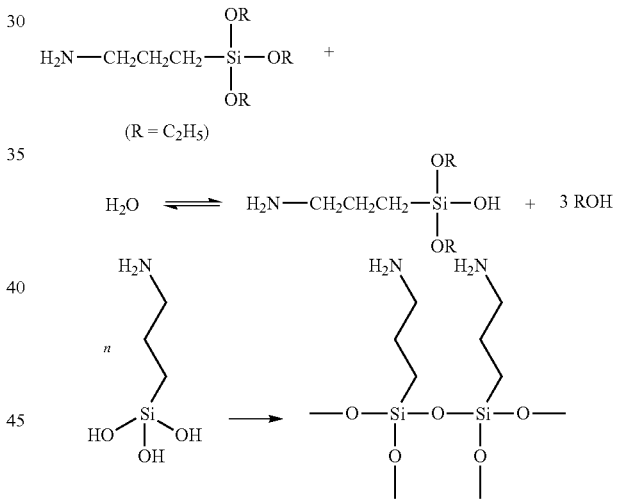

It is desirable in the art to provide an antimicrobial agent which may be easily synthesized, which does not contain chloride ions, and which possesses superior antimicrobial activity.

SUMMARY

Therefore, an object of the disclosure is to provide a method for imparting an article or a hygiene product with antimicrobial activity using an antimicrobial agent which may be easily synthesized, which does not contain chloride ions, and which possesses superior antimicrobial activity.

According to an aspect of the disclosure, there is provided a method for imparting an article or a hygiene product with antimicrobial activity. The method comprises a step of applying an antimicrobial agent including an antimicrobial polyaminosilane to the article or the hygiene product. The antimicrobial polyaminosilane is prepared by subjecting an aminosilane monomer to a hydrolysis and condensation reaction. The antimicrobial polyaminosilane thus prepared is free of halide ions.

According to another aspect of the disclosure, there is provided an article which includes a surface imparted with the antimicrobial activity by the method of the disclosure.

According to further another aspect of the disclosure, there is provided a hygiene product imparted with the antimicrobial activity by the method of the disclosure.

DETAILED DESCRIPTION

The method for imparting an article or a hygiene product with antimicrobial activity according to the disclosure comprises a step of applying an antimicrobial agent including an antimicrobial polyaminosilane to the article or the hygiene product. The antimicrobial polyaminosilane is prepared by subjecting an aminosilane monomer to a hydrolysis and condensation reaction. The antimicrobial polyaminosilane thus prepared is free of halide ions, for example, chloride ions.

The antimicrobial polyaminosilane used in the method of the disclosure is in form of polymeric particulates. In certain embodiments, the polymeric particulates have a size ranging from 1 nm to 10 nm.

In certain embodiment, the polymeric particulates are combined to form aggregates having a size less than 100 nm.

In addition to the antimicrobial polyaminosilane, the antimicrobial agent may further include an additive selected from the group consisting of metal ion, titania, quaternary ammonium salt, chitosan, fluoride, and combinations thereof.

In certain embodiments, the aminosilane monomer is selected from the group consisting of 3-aminopropyltrimethoxysilane, 3-aminopropyltriethoxysilane, triaminofunctional propyltrimethoxysilane, 2-aminoethyl-3-aminopropyltrimethoxysilane, bis(3-triethoxysilylpropyl)amine, diamino/alkyl-functional siloxane, cationic benzylaminofunctional silane, cationic vinylbenzylamino-functional silane, 2-aminoethyl-3-aminopropylmethyldimethoxysilane, 3-aminopropylmethyldiethoxysilane, 3-ureidopropyltriethoxysilane, and combinations thereof.

In certain embodiments, the aminosilane monomer contains an amino group selected from the group consisting of dioctylamino, octylamino, dodecylamino, hexylamino, pyridyl, oleylamino, and combinations thereof.

It should be noted that the antimicrobial polyaminosilane prepared by subjecting the aminosilane monomer to the hydrolysis and condensation reaction contains protonated amino groups carrying positive charges (i.e., $N^+$ ions). Therefore, the antimicrobial polyaminosilane may adsorb onto cell walls of microbe such as fungi, bacteria, and viruses since the cell walls of most of the microbe are negatively charged. The hydrocarbyl groups of the protonated amino groups of the antimicrobial polyaminosilane may then penetrate through the cell walls of the microbe and then through cell membranes of the microbe to cause denaturation of protein contained in the microbe so as to disrupt metabolism of the microbe. Alternatively, the positive charges carried on the protonated amino groups contained in the antimicrobial polyaminosilane may induce production of negative charges on the surfaces of the microbe to cause a non-uniform charge distribution on the surfaces of the microbe, leading to at least one of following results: (1) the charge balance in the electron transport system, the metabolism system, and/or the substance delivery system in the microbe is disrupted to result in coagulation of protein and to disable activity of cell synthase; (2) synthesis of the cell walls is terminated to cause defect of the cell walls; and (3) permeability of the cell membrane is changed and structure of the cell membrane is destroyed to give rise to permeation of cell plasma outwardly through cell membranes and to lead to death of the microbe due to metabolism obstruction or propagation capability loss. Therefore, breeding of the microbe such as fungi, bacteria, and viruses may be effectively inhibited so as to achieve an antimicrobial effect.

In addition, the protonated amino groups contained in the antimicrobial polyaminosilane are used to cause charge imbalance in cells and to destroy the cell walls or the cell membranes, rather than penetrating through the cell walls and the cell membranes to directly participate in an antimicrobial reaction. Therefore, the protonated amino groups contained in the antimicrobial polyaminosilane are not depleted and may maintain antimicrobial activity after the microbe are killed or inhibited. The antimicrobial polyaminosilane may be reused for a long period.

Furthermore, the antimicrobial polyaminosilane prepared by subjecting the aminosilane monomer to the hydrolysis and condensation reaction may be formed with amide linkages (for example, O=C—NH—) and/or Si—O—Si linkages, which may enhance adherence of the antimicrobial polyaminosilane to various substrates. Therefore, the antimicrobial polyaminosilane may be applied and adhered to various substrates. The materials for the substrates include, but are not limited to, metal, alloy, glass, ceramic, glass-ceramic, semiconductive, and polymeric materials, and combinations thereof.

Examples of the polymeric material include, but are not limited to, polyethylene, polypropylene, high density polyethylene, low density polyethylene, linear low density polyethylene, polyvinyl chloride, general purpose polystyrene, expansible polystyrene, high impact polystyrene, styrene-acrylonitrile copolymers, acrylonitrile-butadiene-styrene copolymers, polymethyl methacrylate, ethylene-vinyl acetate copolymers, fiber-reinforced plastic (FRP), polyethylene terephthalate, polybutylene terephthalate, polyamide (Nylon 6.66), polycarbonates, polyacetal, polyphenyleneoxide, polyphenylenesulfide, polyurethanes, polystyrene, polyimide (PI), melamine resin, silica gel, latex, and combinations thereof.

In addition, the antimicrobial polyaminosilane may be applied to display panels of touch type electronic products such as mobile phones and tablet computers so as to provide the touch type electronic products with an antimicrobial effect.

In certain embodiments, other additives for specific requirements may be optionally added to the antimicrobial agent. Examples of the additives include, but are not limited, metals such as zinc, silver, gold, and copper; metal oxides such as titanium dioxide; quaternary ammonium salts; chitosans; fluorine-containing compounds; and combinations thereof.

Specifically, when metals, metal oxides; quaternary ammonium salts; chitosans; or combinations thereof are added to the antimicrobial agent, the antimicrobial effect of the antimicrobial agent may be enhanced since these additives also have antimicrobial activity. When the fluorine-containing compounds are added to the antimicrobial agent, the antimicrobial agent may be further provided with hydrophobic and oleophobic performances because fluorine atoms contained in the fluorine-containing compounds have high cohesion and may reduce surface energy of a coating formed by the antimicrobial agent.

The antimicrobial polyaminosilane contained in the antimicrobial agent used in the method according to the disclosure is prepared by subjecting the aminosilane monomer, which is conventional used as an adhesive agent, a cross-linking agent, or a surface-modifying agent, to a hydrolysis and condensation reaction. As compared with the antimicrobial agent of the prior art, the antimicrobial polyaminosilane used in the method of the disclosure may be prepared relatively simply by subjecting the aminosilane monomer to a hydrolysis and condensation reaction. In addition, since the antimicrobial polyaminosilane does not contain toxic chloride ions, it is environment-friendly. Furthermore, as described above, the protonated amino groups contained in the antimicrobial polyaminosilane are not depleted in use. Therefore, the antimicrobial activity of the antimicrobial polyaminosilane may be maintained for a relatively extended period.

The antimicrobial agent used in the method of the disclosure may be produced by a sol-gel process.

Specifically, one or more of the aforesaid examples of the aminosilane monomer are subjected to a hydrolysis reaction in the presence of water or a solvent containing at least 0.01 wt % water, followed by a condensation reaction in the presence of an acidic or basic solution, thereby preparing the antimicrobial polyaminosilane. The aforesaid hydrolysis and condensation reactions are performed at a temperature from 4° C. to 100° C. and at pH from 2 to 14 for a period not less than 1 second.

The solvent used for the hydrolysis reaction may be a solvent having an alcohol group, a phenyl group, an ether group, a fluoride group, an ester group, or combinations thereof.

The acidic solution used for the condensation reaction may be a sulfuric acid ($H_2SO_4$) solution, a hydrochloric acid (HCl) solution, a nitric acid ($HNO_3$) solution, a citric acid ($C_6H_8O_7$) solution, an oxalic acid ($H_2C_2O_4$) solution, an acetic acid ($CH_3COOH$) solution, a propionic acid ($CH_3CH_2COOH$) solution, a tartaric acid ($C_4H_6O_6$) solution, a maleic acid ($HO_2CCHCHCO_2H$) solution, an ethylenediaminetetraacetic acid (EDTA) solution, a diethylenetriaminepentaacetic acid (DTPA) solution, a solution containing sulfonate, carboxylate, and/or phosphate groups, or combinations thereof.

The basic solution used for the condensation reaction may be a sodium hydroxide (NaOH) solution, an ammonia ($NH_3$) solution, a sodium acetate ($CH_3COONa$) solution, a solution containing sodium, potassium, and/or amino, or combinations thereof.

If required, the aforesaid additives may be added to the antimicrobial agent under stirring to enhance the antimicrobial or other activities.

In use, the antimicrobial agent used in the method of the disclosure is diluted in an organic solvent (for example, alcohol, ketone, ether, or the like) under mechanical blade stirring, magnetic rod stirring, vibration, or roller stirring to prepare a homogeneously diluted solution of the antimicrobial agent. The homogeneously diluted solution is then applied to a surface of an article by dip coating, spin coating, spray coating, roll coating, transfer printing, or the like, followed by drying at a temperature from 20° C. to 350° C. for a period not less than 2 seconds to form an antimicrobial coating layer on the surface of the article so as to impart the article with the antimicrobial activity.

In addition, the antimicrobial agent containing the antimicrobial polyaminosilane may be blended with a resin matrix to prepare an antimicrobial coating, which may be applied to the article. The resin matrix is selected from the group consisting of an acrylic resin, an epoxy acrylate resin, a hydroxyl epoxy resin, an urethane acrylate resin, polyester, polycarbonate, polycaprolactone, polyester acrylate, polyether, polyether acrylate, a phenol-formaldehyde resin, polyurethane, polysaccharide, hydroxyl cellulose, a furan resin, an alkyd resin, a petroleum resin, and combinations thereof.

Alternatively, the antimicrobial agent may be directly applied to the surface of the article via physical vapor deposition or chemical vapor deposition. Examples of the article which may be applied with the antimicrobial agent including the antimicrobial polyaminosilane include, but are not limited to, various polymeric and fabric articles. The amount of the antimicrobial polyaminosilane applied to the article is at least 0.01 wt % based on the weight of the article.

The materials for the polymeric articles include, but are not limited to, polyethylene, polypropylene, high density polyethylene, low density polyethylene, linear low density polyethylene, polyvinyl chloride, general purpose polystyrene, expansible polystyrene, high impact polystyrene, styrene-acrylonitrile copolymers, acrylonitrile-butadiene-styrene copolymers, polymethyl methacrylate, ethylene-vinyl acetate copolymers, fiber-reinforced plastic (FRP), polyethylene terephthalate, polybutylene terephthalate, polyamide (Nylon 6.66), polycarbonates, polyacetal, polyphenyleneoxide, polyphenylenesulfide, polyurethanes, polystyrene, and combinations thereof.

The fabric article may be made from a fiber material selected from the group consisting of cotton, linen, feather, wool, rayon, nylon, polyester silk, mineral wool, glass fiber, cupro, acetate, polyster, polyamide, polyacrylonitrile, and combinations thereof.

In addition, the antimicrobial agent including the antimicrobial polyaminosilane may be added to a solvent so as to prepare a hygiene product which is imparted with the antimicrobial activity. The solvent for preparing the hygiene product may be selected from the group consisting of water, alkane, alkene, alcohol, aldehyde, amine, ester, ether, ketone, aromatic, hydrogenated hydrocarbon, terpene hydrocarbon, halogenated hydrocarbon, heterocyclic compound, nitrogen-containing compound, sulfur-containing compound, benzene, phenol, carbon tetrachloride, carbon disulfide, and combinations thereof.

An example of the disclosure will be described hereinafter. It is to be understood that the example is exemplary and explanatory and should not be construed as a limitation to the disclosure.

EXAMPLE 1

3-aminopropyltrimethoxysilane was subjected to the hydrolysis and condensation reaction described above to prepare an antimicrobial polyaminosilane.

The antimicrobial agent containing the antimicrobial polyaminosilane was applied on substrate pieces to prepare test specimens.

Comparative Example 1

Bare substrate pieces without application of the antimicrobial agent containing the antimicrobial polyaminosilane were used as control specimens.

The test specimens and the control specimens were tested in terms of antimicrobial activity, durability, weather resistance, and chemical resistance.

Microbial species used for the test includes *Escherichia coli* (*E. coli*) and Multiple-resistant *Staphylococcus aureus* (MRSA).

Antimicrobial Activity Test:

*E. coli* in a concentration of $1.0\times10^5$ CFU/ml was applied on ten test specimens and ten control specimens, followed by culture at 35° C. for 24 hours and then rinse with a sterile phosphate buffer (50 ml) to remove dead *E. coli* from the test and control specimens. Similarly, MRSA in a concentration of $1.0\times10^5$ CFU/ml was applied on another ten test specimens and another ten control specimens, followed by culture at 35° C. for 24 hours and then rinse with a sterile phosphate buffer (50 ml) to remove dead MRSA from the test and control specimens. The concentration of the microbial species remained on each of the test and control specimens was determined. Results are shown in Table 1.

TABLE 1

| | *E. coli* | | MRSA | |
|---|---|---|---|---|
| No. | Control (CFU/ml) | Test (CFU/ml) | Control (CFU/ml) | Test (CFU/ml) |
| 1 | $6.0 \times 10^5$ | $1.1 \times 10^2$ | $5.7 \times 10^5$ | $1.8 \times 10^2$ |
| 2 | $6.8 \times 10^5$ | $1.5 \times 10^2$ | $5.8 \times 10^5$ | $2.0 \times 10^2$ |
| 3 | $5.8 \times 10^5$ | $1.0 \times 10^2$ | $5.0 \times 10^5$ | $1.5 \times 10^2$ |
| 4 | $5.3 \times 10^5$ | $1.1 \times 10^2$ | $5.1 \times 10^5$ | $1.1 \times 10^2$ |
| 5 | $5.5 \times 10^5$ | $1.2 \times 10^2$ | $5.0 \times 10^5$ | $1.5 \times 10^2$ |
| 6 | $5.5 \times 10^5$ | $1.2 \times 10^2$ | $5.5 \times 10^5$ | $2.2 \times 10^2$ |
| 7 | $5.3 \times 10^5$ | $1.8 \times 10^2$ | $5.5 \times 10^5$ | $2.0 \times 10^2$ |
| 8 | $5.8 \times 10^5$ | $1.6 \times 10^2$ | $5.1 \times 10^5$ | $1.0 \times 10^2$ |
| 9 | $5.8 \times 10^5$ | $1.3 \times 10^2$ | $5.3 \times 10^5$ | $2.0 \times 10^2$ |
| 10 | $5.8 \times 10^5$ | $1.0 \times 10^2$ | $5.8 \times 10^5$ | $2.2 \times 10^2$ |

Durability Test:

Each set of the test specimens and the control specimens were treated with one of the following three processes: 1) rubbing the surface of each of the test specimens and the control specimens back and forth once with a #0000 steel wool pad having a load of 200 g; 2) wiping the surface of each of the test specimens and the control specimens with a dry clean cloth 5000 times; and 3) wiping the surface of each of the test specimens and the control specimens with a wet clean cloth 5000 times. *E. coli* in a concentration of $1\times10^5$ CFU/ml was applied on each set of the test specimens and the control specimens after one of the aforesaid processes, followed by culture at 35° C. for 24 hours and then rinse with a sterile phosphate buffer (50 ml) to remove dead *E. coli* from the specimens. Similarly, MRSA in a concentration of $1\times10^5$ CFU/ml was applied on each set of the test specimens and the control specimens after one of the aforesaid processes, followed by culture at 35° C. for 24 hours and then rinse with a sterile phosphate buffer (50 ml) to remove dead MRSA from the specimens. The concentration of the microbial species remained on each of the specimens was determined. Results are shown in Table 2.

TABLE 2

| | *E. coli* | | | MRSA | | |
|---|---|---|---|---|---|---|
| Process Nos. | Control (CFU/ml) | Test (CFU/ml) | Appearance | Control (CFU/ml) | Test (CFU/ml) | Appearance |
| 1 | $4.5 \times 10^5$ | $1.1 \times 10^2$ | No stripping | $5.7 \times 10^5$ | $2.0 \times 10^2$ | No stripping |
|   | $5.5 \times 10^5$ | $1.4 \times 10^2$ | No stripping | $5.8 \times 10^5$ | $1.8 \times 10^2$ | No stripping |
|   | $5.0 \times 10^5$ | $1.5 \times 10^2$ | No stripping | $5.5 \times 10^5$ | $1.5 \times 10^2$ | No stripping |
| 2 | $5.1 \times 10^5$ | $1.1 \times 10^2$ | No stripping | $5.5 \times 10^5$ | $1.4 \times 10^2$ | No stripping |
|   | $5.5 \times 10^5$ | $1.5 \times 10^2$ | No stripping | $5.6 \times 10^5$ | $1.5 \times 10^2$ | No stripping |
|   | $5.0 \times 10^5$ | $1.1 \times 10^2$ | No stripping | $5.2 \times 10^5$ | $1.2 \times 10^2$ | No stripping |
| 3 | $5.5 \times 10^5$ | $1.8 \times 10^2$ | No stripping | $6.3 \times 10^5$ | $2.5 \times 10^2$ | No stripping |
|   | $5.2 \times 10^5$ | $1.5 \times 10^2$ | No stripping | $6.1 \times 10^5$ | $1.8 \times 10^2$ | No stripping |
|   | $4.5 \times 10^5$ | $1.0 \times 10^2$ | No stripping | $6.3 \times 10^5$ | $2.0 \times 10^2$ | No stripping |

As shown in Table 2, there is no stripping of the antimicrobial agent from the surfaces of the test specimens, and satisfactory antimicrobial effect may be still achieved for the test specimens after the treatment with any one of the aforesaid processes.

Weather Resistance Test:

Each set of the test specimens and the control specimens were treated with one of the following three conditions: 1) a temperature of 90° C., a relative moisture of 0%, and a period of 100 hours; 2) a temperature of 40° C., a relative moisture of 80%, and a period of 120 hours; and 3) a temperature of 55° C., a relative moisture of 93%, and a period of 240 hours. *E. coli* in a concentration of $1\times10^5$ CFU/ml was applied on each set of the test specimens and the control specimens after the treatment with one of the aforesaid conditions, followed by culture at 35° C. for 24 hours and then rinse with a sterile phosphate buffer (50 ml) to remove dead *E. coli* from the specimens. Similarly, MRSA in a concentration of $1\times10^5$ CFU/ml was applied on each set of the test specimens and the control specimens after the treatment with one of the aforesaid conditions, followed by culture at 35° C. for 24 hours and then rinse with a sterile phosphate buffer (50 ml) to remove dead MRSA from the specimens. The concentration of the microbial species remained on each of the specimens was determined. Results are shown in Table 3.

TABLE 3

| Condition Nos. | E. coli Control (CFU/ml) | Test (CFU/ml) | Appearance | MRSA Control (CFU/ml) | Test (CFU/ml) | Appearance |
|---|---|---|---|---|---|---|
| 1 | $5.5 \times 10^5$ | $1.4 \times 10^2$ | No change | $5.5 \times 10^5$ | $1.0 \times 10^2$ | No change |
|   | $5.5 \times 10^5$ | $1.4 \times 10^2$ | No change | $5.6 \times 10^5$ | $1.5 \times 10^2$ | No change |
|   | $5.0 \times 10^5$ | $1.1 \times 10^2$ | No change | $5.5 \times 10^5$ | $1.2 \times 10^2$ | No change |
| 2 | $5.1 \times 10^5$ | $1.1 \times 10^2$ | No change | $5.5 \times 10^5$ | $1.3 \times 10^2$ | No change |
|   | $5.5 \times 10^5$ | $1.5 \times 10^2$ | No change | $5.7 \times 10^5$ | $1.5 \times 10^2$ | No change |
|   | $5.4 \times 10^5$ | $1.2 \times 10^2$ | No change | $5.2 \times 10^5$ | $1.2 \times 10^2$ | No change |
| 3 | $5.5 \times 10^5$ | $1.5 \times 10^2$ | No change | $5.3 \times 10^5$ | $1.2 \times 10^2$ | No change |
|   | $5.2 \times 10^5$ | $1.0 \times 10^2$ | No change | $5.1 \times 10^5$ | $1.5 \times 10^2$ | No change |
|   | $5.5 \times 10^5$ | $1.4 \times 10^2$ | No change | $5.3 \times 10^5$ | $1.0 \times 10^2$ | No change |

As shown in Table 3, there is no substantial change in appearances of the test specimens when observed the test specimens put on a white paper, and satisfactory antimicrobial effect may be still achieved for the test specimens after the treatment with one of the aforesaid conditions.

Chemical Resistance Test:

The test specimens and the control specimens were immersed in isopropyl alcohol in a container for 48 hours, and were then taken from the container and dried. E. coli in a concentration of $1 \times 10^5$ CFU/ml was applied on each of the test specimens and the control specimens, followed by culture at 35° C. for 24 hours and then rinse with a sterile phosphate buffer (50 ml) to remove dead E. coli from the specimens. Similarly, MRSA in a concentration of $1 \times 10^5$ CFU/ml was applied on each of the test specimens and the control specimens, followed by culture at 35° C. for 24 hours and then rinse with a sterile phosphate buffer (50 ml) to remove dead MRSA from the specimens. The concentration of the microbial species remained on each of the specimens was determined. Results are shown in Table 4.

TABLE 4

| E. coli Control (CFU/ml) | Test (CFU/ml) | Appearance | MRSA Control (CFU/ml) | Test (CFU/ml) | Appearance |
|---|---|---|---|---|---|
| $4.5 \times 10^5$ | $1.0 \times 10^2$ | No change | $5.5 \times 10^5$ | $1.3 \times 10^2$ | No change |
| $4.5 \times 10^5$ | $1.0 \times 10^2$ | No change | $5.2 \times 10^5$ | $1.0 \times 10^2$ | No change |
| $5.0 \times 10^5$ | $1.8 \times 10^2$ | No change | $5.5 \times 10^5$ | $1.2 \times 10^2$ | No change |

As shown in Table 4, there is no substantial change in appearances of the test specimens when observed the test specimens put on a white paper, and satisfactory antimicrobial effect may be still achieved for the test specimens after the treatment with isopropyl alcohol.

It is indicated from the results shown in Tables 1-4 that the antimicrobial agent including the antimicrobial polyaminosilane applied on the test specimens remained satisfactory antimicrobial effect and do not have stripping or discolored appearance in the durability, weather resistance, and chemical resistance tests. Specifically, the survival rates of E. coli and MRSA on the test specimens applied with the antimicrobial agent including the antimicrobial polyaminosilane are less than 0.0001%.

In addition, the antimicrobial agent containing the antimicrobial polyaminosilane was subjected to an antibacterial test (JIS Z2801) and an antifungal test (ASTM G21) by SGS Taiwan Ltd. The results are shown in Tables 5-7.

TABLE 5

| | Microbial species E. coli ATCC 8739 | | | |
|---|---|---|---|---|
| Treatment | $CFU/cm^2$ | LOG | R | Antimicrobial rate |
| A | $8.9 \times 10^3$ | 3.94 | 5.33 | 99.999% |
| B | $6.7 \times 10^5$ | 5.82 | | |
| C | 3.10 | 0.49 | | |

TABLE 6

| | Microbial species MRSA ATCC 33591 | | | |
|---|---|---|---|---|
| Treatment | $CFU/cm^2$ | LOG | R | Antimicrobial rate |
| A | $1.2 \times 10^4$ | 4.07 | 5.87 | 99.999% |
| B | $3.7 \times 10^6$ | 6.56 | | |
| C | 5.00 | 0.69 | | |

A: The control specimen immediately after the inoculation of the microbial species B: The control specimen after culture for 24 hours C: The test specimen, which is coated with the antimicrobial agent containing the antimicrobial polyaminosilane, after culture for 24 hours.

R (antimicrobial activity value)=log B−log C. An antimicrobial activity value (R) not less than 2 indicates that the antimicrobial effect is confirmed.

TABLE 7

Propagation and Distribution of microbial species after culture for 28 days

| Microbial species | Rate |
|---|---|
| *Aspergillus niger* ATCC 9642 | 0 |
| *Penicillium pinophilum* ATCC 11797 | |
| *Chaetomium globosum* ATCC 6205 | |
| *Gliocladium virens* ATCC 9645 | |
| *Aureobasidium pullulans* ATCC 15233 | |
| Rating: | |
| Propagation of microbial species | |
| None | 0 |
| Propagation ratio: <10% | 1 |
| Propagation ratio: 10%-30% | 2 |
| Propagation ratio: 30%-60% | 3 |
| Propagation ratio: 60%-100% | 4 |

It is indicated from the results shown in Tables 5-7 that in addition to *E. coli* and MRSA, the antimicrobial agent containing the antimicrobial polyaminosilane may also effectively inhibit the propagation of other microbial species. In addition, the antimicrobial ratio of the antimicrobial agent containing the antimicrobial polyaminosilane to these microbial species may be as high as 99.999%.

Comparative Example 2

Tetraethyl orthosilicate (an organosilane containing no amino) was subjected to an antibacterial test (JIS Z2801). The results are shown in Table 8.

TABLE 8

| Microbial species | Average of the number of viable cells of bacteria on blank sample (CFU/cm$^2$) | Log average of the number of viable cells of bacteria on blank sample | Average of the number of viable cells of bacteria on test sample after 24 hours (CFU/cm$^2$) | Log average of the number of viable cells of bacteria on test sample after 24 hours | Antibacterial activity (R) |
|---|---|---|---|---|---|
| *E. coli* | 9.47 × 10$^5$ | 5.98 | 1.00 × 10$^6$ | 6.00 | ≤0 |

It is shown from the results of Table 8 that tetraethyl orthosilicate, which does not contain amino group, does not have antibacterial activity (i.e., R=0). Contrarily, as shown in Tables 5 and 6, the R values for *E. coli* and MRSA determined for the antimicrobial agent containing the antimicrobial polyaminosilane are 5.33 and 5.87, respectively, indicating superior antibacterial activity, and the antimicrobial rates achieved thereby are almost 100.00%.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

The invention claimed is:

1. A method for inhibiting propagation of microbial species comprising:
   contacting the microbial species with an antimicrobial agent comprising an antimicrobial polyaminosilane,
   wherein the antimicrobial polyaminosilane is prepared by a process of subjecting only an aminosilane monomer to a hydrolysis and a condensation reaction so that the antimicrobial polyaminosilane has a repeating unit containing only aminosilane and is free of chloride ions,
   the antimicrobial polyaminosilane contains protonated amino groups carrying positive charges,
   the antimicrobial polyaminosilane is in a form of polymeric particulates, and
   the polymeric particulates are combined to form aggregates having a size less than 100 nm.

2. The method according to claim 1, wherein the aminosilane monomer is selected from the group consisting of 3-aminopropyltrimethoxysilane, 3-aminopropyltriethoxysilane, triamino-functional propyltrimethoxysilane, 2-aminoethyl-3-aminopropyltrimethoxysilane, bis(3-triethoxysilylpropyl)amine, diamino/alkyl-functional siloxane, cationic benzylamino-functional silane, cationic vinylbenzylamino-functional silane, 2-aminoethyl-3-aminopropylmethyldimethoxysilane, 3-aminopropylmethyldiethoxysilane, 3-ureidopropyltriethoxysilane, and combinations thereof.

3. The method according to claim 1, wherein the aminosilane monomer contains an amino group selected from the group consisting of dioctylamino, octylamino, dodecylamino, hexylamino, pyridyl, oleylamino, and combinations thereof.

4. The method according to claim 3, wherein the polymeric particulates have a size ranging from 1 nm to 10 nm.

5. The method according to claim 3, wherein the antimicrobial agent further includes an additive selected from the group consisting of metal ion, titania, quaternary ammonium salt, chitosan, fluoride, and combinations thereof.

6. The method according to claim 3, wherein the antimicrobial polyaminosilane is free of halide ions.

7. The method according to claim 3, wherein the hydrolysis reaction is conducted in the presence of water or a solvent containing at least 0.01 wt % water, and the condensation reaction is conducted in the presence of an acidic or basic solution.

\* \* \* \* \*